US008067601B2

(12) United States Patent
Bonard et al.

(10) Patent No.: US 8,067,601 B2
(45) Date of Patent: Nov. 29, 2011

(54) 1-[2-(4-BENZYL-4-HYDROXY-PIPERIDIN-1-YL)-ETHYL]-3-(2-METHYL-QUINOLIN-4-YL)- UREA AS CRYSTALLINE SULFATE SALT (75) Inventors: Jean-Michel Bonard, Villeurbanne (FR); Stephan Buchmann, Basel (CH); Stéphane Redey, Mulhouse (FR); Bertrand Woinet, Lyons (FR)

(73) Assignee: Actelion Pharmaceticals Ltd., Allschwil (CH)

( * ) Notice: Subject to any disclaimer, the term of this patent is extended or adjusted under 35 U.S.C. 154(b) by 1077 days.

(21) Appl. No.: 11/577,064

(22) PCT Filed: Oct. 11, 2005

(86) PCT No.: PCT/IB2005/053340
§ 371 (c)(1),
(2), (4) Date: Oct. 9, 2007

(87) PCT Pub. No.: WO2006/040728
PCT Pub. Date: Apr. 20, 2006

(65) Prior Publication Data
US 2009/0023775 A1    Jan. 22, 2009

(30) Foreign Application Priority Data
Oct. 12, 2004  (WO) ................. PCT/EP2004/011410

(51) Int. Cl.
*C07D 295/00*  (2006.01)
(52) U.S. Cl. ................................... 546/162
(58) Field of Classification Search ............ 546/162
See application file for complete search history.

(56) References Cited

U.S. PATENT DOCUMENTS

| 6,331,541 | B1 | 12/2001 | Ko et al. |
| 2007/0043081 | A1 | 2/2007 | Bur et al. |

FOREIGN PATENT DOCUMENTS

| EP | 428434 | 5/1991 |
| WO | WO 99/21835 | 5/1999 |
| WO | WO 99/40192 | 8/1999 |
| WO | WO 01/09088 | 2/2001 |
| WO | WO 01/45694 | 6/2001 |
| WO | WO 01/45700 | 6/2001 |
| WO | WO 01/45711 | 6/2001 |
| WO | WO 01/66143 | 9/2001 |
| WO | WO 02/00606 | 1/2002 |
| WO | WO 02/02530 | 1/2002 |
| WO | WO 02/47456 | 6/2002 |
| WO | WO 02/47687 | 6/2002 |
| WO | WO 02/058702 | 8/2002 |
| WO | WO 02/076979 | 10/2002 |
| WO | WO 02/078641 | 10/2002 |
| WO | WO 02/078707 | 10/2002 |
| WO | WO 02/079155 | 10/2002 |
| WO | WO 02/079188 | 10/2002 |
| WO | WO 02/089740 | 11/2002 |
| WO | WO 02/089785 | 11/2002 |
| WO | WO 02/089792 | 11/2002 |
| WO | WO 02/089793 | 11/2002 |
| WO | WO 02/090337 | 11/2002 |
| WO | WO 02/090348 | 11/2002 |
| WO | WO 02/090353 | 11/2002 |
| WO | WO 03/048154 A1 | 6/2003 |
| WO | WO 2004/026836 | * 4/2004 |
| WO | WO 2004/043366 | 5/2004 |
| WO | WO 2004/043368 | 5/2004 |
| WO | WO 2004/043369 | 5/2004 |
| WO | WO 2004/043463 | 5/2004 |
| WO | WO 2004/043917 | 5/2004 |
| WO | WO 2004/043948 | 5/2004 |
| WO | WO 2004/073634 | 9/2004 |
| WO | WO 2004/099179 | 11/2004 |

OTHER PUBLICATIONS

Clozel et al., The Journal of Pharmacology and Experimental Therapeutics, vol. 311, pp. 204-212 (2004).
Ames, R.S. et al., "Human urotensin-II is a potent vasoconstrictor and agonist for the orphan receptor GPR14" Nature (1999), 401, pp. 282-286.
Bern, H.A. et al., "Neurohormones from fish tails: the caudal neurosecretory system. I. Urophysiology and the caudal neurosecretory system of fishes", Recent Prog. Horm. Res., (1985), 41, pp. 533-552.
Breu, V. et al., In vitro characterization of Ro-46-2005, a novel synthetic non-peptide antagonist of $ET_A$ and $ET_B$ receptors., FEBS Lett., (1993), 334, pp. 210-214. Cheung, B.M. et al., "Plasma concentration of urotensin II is raised in hypertension", J. Hypertens., (2004), 22, pp. 1341-1344.
Douglas, S.A., et al., "Differential vasoconstrictor activity of human urotensin-II in vascular tissue isolated from the rat, mouse, dog, pig, marmoset and cynomolgus monkey", Br. J. Pharmacol., (2000), 131, pp. 1262-1274.
Douglas, S.A. et al., "Human urotensin-II is a potent vasoactive peptide: pharmacological characterization in the rat, mouse, dog and primate", J. Cardiovasc. Pharmacol., (2000), 36, Suppl 1:S163-S166.
Garlton, J., et al., "Central effects of urotensin-II following ICV administration in rats", Psychopharmacology (Berlin), (2001), 155, pp. 426-433.
Heller, J. et al., "Increased urotensin II plasma levels in patients with cirrhosis and portal hypertension", J. Hepatol., (2002), 37, pp. 767-772.
Liu, Q. et al., "Identification of urotension II as the endogenous ligand for the orphan G-protein-coupled receptor GPR14", Biochem. Biophys. Res. Commun., (1999), 266, pp. 174-178.

(Continued)

*Primary Examiner* — Nizal Chandrakumar
(74) *Attorney, Agent, or Firm* — Hoxie & Associates (57) ABSTRACT

The invention relates to 1-[2-(4-benzyl-4-hydroxy-piperidin-1-yl)-ethyl]-3-(2-methyl-quinolin-4-yl)-urea as a crystalline, stoichiometrically defined and non-hygroscopic sulfate salt and a process for its preparation. Further, the present invention relates to the use of said 1-[2-(4-benzyl-4-hydroxy-piperidin-1-yl)-ethyl]-3-(2-methyl-quinolin-4-yl)-urea as a crystalline, stoichiometrically defined and non-hygroscopic sulfate salt alone or in combination with other compounds. Further, the present invention relates to formulations of said 1-[2-(4-benzyl-4-hydroxy-piperidin-1-yl)-ethyl]-3-(2-methyl-quinolin-4-yl)-urea as a crystalline, stoichiometrically defined and non-hygroscopic sulfate salt in the preparation of pharmaceutical compositions. The invention also relates to the use of such sulfate salts in formulations as neurohormonal antagonists.

4 Claims, 3 Drawing Sheets

OTHER PUBLICATIONS

Malinowski, M., et al., "A Convenient Preparation of 4-Pyridinamine Derivatives", J. Prakt, Chem., (1988), 330, pp. 154-158.

Mori, M. et al., "Urotensin II is the endogenous ligand of a G-protein-coupled orphan receptor, SENR (GPR14)", Biochem. Biophys. Res. Commun., (1999), 265, pp. 123-129.

"Protective Groups in Organic Synthesis", T.W. Greene, P.G.M. Wuts, Wiley-Interscience, (1999).

Russell, F.D., et al., "Cardiostimulant effects of urotensin-II in human heart in vitro", Br. J. Pharmacol., (2001), 132, pp. 5-9.

Shenouda, S. et al., "Localization of urotensin-II immunoreactivity in normal human kidneys and renal carcinoma", J. Histochem. Cytochem, (2002), 50, pp. 885-889.

Silvestre, R.A., et al., "Inhibition of insulin release by urotensin II—a study on the perfused rat pancreas", Horm Metab Res, (2001), 33, pp. 379-381.

Takahashi, K. et al., "Expression of utotensin II and urotensin II receptor mRNAs in various human tumor cell lines and secretion of urotensin II-like immunoreactivity b SW-13 adrenocortical carcinoma cells", Peptides, (2001), 22, pp. 1175-1179.

Takahashi, K. et al., "Expression of urotensin II and its receptor in adrenal tumors and stimulation of proliferation of cultured tumor cells by urotensin II", Peptides, (2003), 24, pp. 301-306.

Totsune, K. et al., "Role of urotensin II in patients on dialysis", Lancent, (2001), 358, pp. 810-811.

Totsune, K. et al., "Increased plasma urotensin II levels in patients with diabetes mellitus" Clin. Sci., (2003), 104, pp. 1-5.

Tsandis, A. et al., "Urotensin II stimulates collagen synthesis of cardiac fibroblasts and hypertrophic signaling in cardiomyocytes via G(alpha)q- and Ras-dependent pathways", J. Am. Coll. Cardiol., (2001), 37, p. 164A.

Zou, Y. et al., "Urotensin II induces hypertrophic responses in cultured cardiomyocytes from neonatal rats" FEBS Lett., (2001), 508, pp. 57-60.

* cited by examiner

1-[2-(4-BENZYL-4-HYDROXY-PIPERIDIN-1-YL)-ETHYL]-3-(2-METHYL-QUINOLIN-4-YL)- UREA AS CRYSTALLINE SULFATE SALT

The present invention relates to 1-[2-(4-benzyl-4-hydroxy-piperidin-1-yl)-ethyl]-3-(2-methyl-quinolin-4-yl)-urea as crystalline, stoichiometrically defined and non-hygroscopic sulfate salt add a process for its preparation. Further, the present invention relates to the use of said 1-[2-(4-benzyl-4-hydroxy-piperidin-1-yl)-ethyl]-3-(2-methyl-quinolin-4-yl)-urea as crystalline, stoichiometrically defined and non-hygroscopic sulfate salt alone or in combination with other compounds. The present invention also relates to compositions containing said 1-[2-(4-benzyl-4-hydroxy-piperidin-1-yl)-ethyl]-3-(2-methyl-quinolin-4-yl)-urea as crystalline, stoichiometrically defined and non-hygroscopic sulfate salt and inert carrier material which are useful as urotensin-II antagonist.

1-[2-(4-Benzyl-4-hydroxy-piperidin-1-yl)-ethyl]-3-(2-methyl-quinolin-4-yl)-urea of formula I as well as the process for its preparation as free base is known from WO-2004026836. 1-[2-(4-Benzyl-4-hydroxy-piperidin-1-yl)-ethyl]-3-(2-methyl-quinolin-4-yl)-urea of formula I has been shown to be a potent urotensin II receptor antagonist [Martine Clozel et al. in J. Pharmcol. Exp. Ther. 2004, 311, 204-212].

I

1-[2-(4-Benzyl-4-hydroxy-piperidin-1-yl)-ethyl]-3-(2-methyl-quinolin-4-yl)-urea of formula I as free base has the disadvantages that it is hygroscopic, its colour changes at higher temperature and higher humidity and it agglomerates to a substance cake under these conditions. Therefore, the said compound of formula I as free base is not suitable as a pharmaceutical product since it is not easy to handle in pharmaceutical preparations. In addition, large scale production and storage of the said compound of formula I causes problems due to the properties mentioned above.

An object of the present invention is to provide 1-[2-(4-benzyl-4-hydroxy-piperidin-1-yl)-ethyl]-3-(2-methyl-quinolin-4-yl)-urea of formula I in a stoichiometrically defined and non-hygroscopic crystalline form which shows improved properties suitable for a pharmaceutical product, pharmaceutical preparations, production in large scale and storage.

The present invention relates to 1-[2-(4-benzyl-4-hydroxy-piperidin-1-yl)-ethyl]-3-(2-methyl-quinolin-4-yl)-urea of formula I as a sulfate trihydrate. A sulfate salt of 1-[2-(4-benzyl-4-hydroxy-piperidin-1-yl)-ethyl]-3-(2-methyl-quinolin-4-yl)-urea of formula I is described by [Martine Clozel et. al., J Pharmacol Exp Ther. 2004; DOI:10.1124/jpet.104.068320] but no procedure for its preparation has been disclosed.

The present invention also relates to 1-[2-(4-benzyl-4-hydroxy-piperidin-1-yl)-ethyl]-3-(2-methyl-quinolin-4-yl)-urea of formula I as a sulfate dihydrate.

The present invention also relates to a process for preparing 1-[2-(4-benzyl-4-hydroxy-piperidin-1-yl)-ethyl]-3-(2-methyl-quinolin-4-yl)-urea of formula I as stoichiometrically defined and non-hygroscopic sulfate salt which process comprises a) mixing 1-[2-(4-benzyl-4-hydroxy-piperidin-1-yl)-ethyl]-3-(2-methyl-quinolin-4-yl)-urea of formula I and an organic solvent and adding a solution of sulfuric acid in water, or a solution of sulfuric acid in a mixture of water and an organic solvent, and stirring the mixture; or b) mixing 1-[2-(4-benzyl-4-hydroxy-piperidin-1-yl)-ethyl]-3-(2-methyl-quinolin-4-yl)-urea of formula I and a mixture of an organic solvent and water and adding a solution of sulfuric acid in water, or a solution of sulfuric acid in a mixture of water and an organic solvent, and stirring the mixture; or c) adding 1-[2-(4-benzyl-4-hydroxy-piperidin-1-yl)-ethyl]-3-(2-methyl-quinolin-4-yl)-urea of formula I as a solid, or dissolved in a mixture of an organic solvent and water to a solution of sulfuric acid in water or to a solution of sulfuric acid in a mixture of water and an organic solvent, and stirring the mixture; or d) adding 1-[2-(4-benzyl-4-hydroxy-piperidin-1-yl)-ethyl]-3-(2-methyl-quinolin-4-yl)-urea of formula I as a solid, or dissolved in an organic solvent to a solution of sulfuric acid in water or to a solution of sulfuric acid in a mixture of water and an organic solvent, and stirring the mixture; or e) hydration of a non-defined 1-[2-(4-benzyl-4-hydroxy-piperidin-1-yl)-ethyl]-3-(2-methyl-quinolin-4-yl)-urea sulfate hydrate by stirring in water, in a mixture of water and an organic solvent, or by exposure to an atmosphere of controlled relative humidity.

According to a preferred embodiment of this process, the sulfate salt of 1-[2-(4-benzyl-4-hydroxy-piperidin-1-yl)-ethyl]-3-(2-methyl-quinolin-4-yl)-urea of formula I is 1-[2-(4-benzyl-4-hydroxy-piperidin-1-yl)-ethyl]-3-(2-methyl-quinolin-4-yl)-urea sulfate trihydrate.

Further, the present invention relates to 1-[2-(4-benzyl-4-hydroxy-piperidin-1-yl)-ethyl]-3-(2-methyl-quinolin-4-yl)-urea of formula I as stoichiometrically defined and non-hygroscopic sulfate salt obtainable by the process mentioned above.

Further, the present invention relates to pharmaceutical compositions comprising 1-[2-(4-benzyl-4-hydroxy-piperidin-1-yl)-ethyl]-3-(2-methyl-quinolin-4-yl)-urea of formula I as stoichiometrically defined and non-hygroscopic sulfate salt as mentioned above and inert carrier material Further, the present invention relates to 1-[2-(4-benzyl-4-hydroxy-piperidin-1-yl)-ethyl]-3-(2-methyl-quinolin-4-yl)-urea salts as mentioned above and their use as medicaments.

Because of their ability to inhibit the actions of urotensin II, 1-[2-(4-benzyl-4-hydroxy-piperidin-1-yl)-ethyl]-3-(2-methyl-quinolin-4-yl)-urea salts as described above can be used for treatment of diseases which are associated with an increase in vasoconstriction, proliferation or other disease states associated with the actions of urotensin II. Examples of such diseases are hypertension, atherosclerosis, angina or myocardial ischemia, congestive heart failure, cardiac insufficiency, cardiac arrhythmias, renal ischemia, chronic kidney disease, renal failure, stroke, cerebral vasospasm, cerebral ischemia, dementia, migraine, subarachnoidal hemorrhage, diabetes, diabetic arteriopathy, diabetic nephropathy, connective tissue diseases, cirrhosis, asthma, chronic obstructive pulmonary disease, high-altitude pulmonary edema, Raynaud's syndrome, portal hypertension, thyroid dysfunction, pulmonary edema, pulmonary hypertension, or pulmonary fibrosis. They can also be used for prevention of restenosis after balloon or stent angioplasty, for the treatment of cancer, prostatic hypertrophy, erectile dysfunction, hearing loss, amaurosis, chronic bronchitis, asthma, gram negative septicemia, shock, sickle cell anemia, sickle cell acute chest syndrome, glomerulonephritis, renal colic, glaucoma, therapy and prophylaxis of diabetic complications, complications of vascular or cardiac surgery or after organ transplantation, complications of cyclosporin treatment, pain, addictions, schizophrenia, Alzheimer's disease, anxiety, obsessive-compulsive behavior, epileptic seizures, stress, depression, dementias, neuromuscular disorders, neurodegenerative diseases, as well as, other diseases related to a dysregulation of urotensin II or urotensin II receptors.

These compositions may be administered in enteral or oral form e.g. as tablets, dragees, gelatine capsules, emulsions, solutions or suspensions, in nasal form like sprays and aerosols, or rectally in form of suppositories. 1-[2-(4-Benzyl-4-hydroxy-piperidin-1-yl)-ethyl]-3-(2-methyl-quinolin-4-yl)-urea salts as mentioned above may also be administered in intramuscular, parenteral or intravenous form, e.g. in form of injectable solutions.

These pharmaceutical compositions may contain 1-[2-(4-benzyl-4-hydroxy-piperidin-1-yl)-ethyl]-3-(2-methyl-quinolin-4-yl)-urea salts as mentioned above in combination with inorganic and/or organic excipients, which are usual in the pharmaceutical industry, like lactose, maize or derivatives thereof, talcum, stearic acid or salts of these materials.

For gelatine capsules vegetable oils, waxes, fats, liquid or half-liquid polyols etc. may be used. For the preparation of solutions and sirups e.g. water, polyols, saccharose, glucose etc. are used. Injectables are prepared by using e.g. water, polyols, alcohols, glycerin, vegetable oils, lecithin, liposomes etc. Suppositories are prepared by using natural or hydrogenated oils, waxes, fatty acids (fats), liquid or half-liquid polyols etc.

The compositions may contain in addition preservatives, stabilisation improving substances, viscosity improving or regulating substances, solubility improving substances, sweeteners, dyes, taste improving compounds, salts to change the osmotic pressure, buffer, anti-oxidants etc.

1-[2-(4-Benzyl-4-hydroxy-piperidin-1-yl)-ethyl]-3-(2-methyl-quinolin-4-yl)-urea salts as mentioned above may also be used in combination with one or more other therapeutically useful substances e.g. with α- and β-blockers like phentolamine, phenoxybenzamine, atenolol, propranolol, timolol, metoprolol, carteolol, carvedilol, etc.; with vasodilators like hydralazine, minoxidil, diazoxide, flosequinan, etc.; with calcium-antagonists like diltiazem, nicardipine, nimodipine, verapamil, nifedipine, etc.; with angiotensin converting enzyme-inhibitors like cilazapril, captopril, enalapril, lisinopril etc.; with potassium channel activators like pinacidil, chromakalim, etc.; with angiotensin receptor antagonists like losartan, valsartan, candesartan, irbesartan, eprosartan, telmisartan, and tasosartan, etc.; with diuretics like hydrochlorothiazide, chlorothiazide, acetolamide, bumetanide, furosemide, metolazone, chlortalidone, etc.; with sympatholytics like methyldopa, clonidine, guanabenz, reserpine, etc.; with endothelin receptor antagonists like bosentan, clazosentan, tezosentan, darusentan, atrasentan, enrasentan, or sitaxsentan, etc.; with anti-hyperlipidemic agents like lovastatin, pravastatin, fluvastatin, atorvastatin, cerivastatin, simvastatin, etc.; and other therapeutics which serve to treat high blood pressure, vascular disease or other disorders listed above.

The dosage may vary within wide limits but should be adapted to the specific situation. In general the dosage given daily in oral form should be between about 3 mg and about 3 g, preferably between about 5 mg and about 1 g, especially preferred between 10 mg and 300 mg, per adult with a body weight of about 70 kg. The dosage should be administered preferably in 1 to 3 doses of equal weight per day. As usual children should receive lower doses which are adapted to body weight and age.

The present invention also relates to compositions containing amorphous parts of 1-[2-(4-benzyl-4-hydroxy-piperidin-1-yl)-ethyl]-3-(2-methyl-quinolin-4-yl)-urea salts as mentioned above.

The term "crystallinity" or "crystalline" is used to describe the part of crystalline material compared to amorphous material and is estimated eg. by the line shape and the background intensity in X-ray diffraction patterns.

According to these methods, a crystallinity of 90% to 100% is estimated. In a more preferred embodiment the crystallinity is within the range of 92% to 100%. In the most preferred embodiment the crystallinity is within the range of 95% to 100%.

The term "organic solvents", as used within the present invention, means solvents or mixtures of solvents, such as $C_{1-4}$-alkanol ($CH_3OH$, $C_2H_5OH$, n-$C_3H_7OH$, I—$C_3H_7OH$, n-$C_4H_9OH$, i-$C_4H_9OH$, t-$C_4H_9OH$), ketones (acetone, ethylmethylketone, methylisobutylketone), ethers (diethylether, tetrahydrofurane, 1,4-dioxane, methyl-tert. butylether) or acetonitrile. Preferred "organic solvents" are $CH_3OH$, $C_2H_5OH$, n-$C_3H_7OH$, i-$C_3H_7OH$ and acetone. Most preferred "organic solvents" are $CH_3OH$, $C_2H_5OH$, i-$C_3H_7OH$ and acetone.

The term "solution of sulfuric acid" as used within the present invention, means solutions of sulfuric acid in water, or a solution of sulfuric acid in a mixture of water and an organic solvent, preferably aqueous solutions. Sulfuric acid solutions are in the concentration range of 0.01 to 10 mol/L, more preferred in the concentration range of 0.1 to 5 mol/L, most preferred in the concentration range of 0.2 to 2 mol/L.

The term "stoichiometrically defined crystalline form", as used within the present invention, means crystalline compounds as described before that contain 1 [2 (4 benzyl-4-hydroxy-piperidin-1-yl)-ethyl]-3-(2-methyl-quinolin-4-yl)-urea of Formula I, sulfuric acid and water in a defined molecular ratio X:Y:Z, whereby X and Y represent 1, and Z represents the numbers 0 to 4. In a more preferred embodiment Z represents the numbers 0 to 3. In the most preferred embodiment Z represents the numbers 2 or 3.

The foregoing general description of the invention will now be further illustrated with a number of non-limiting examples.

EXAMPLES ACCORDING TO THE INVENTION

| LIST OF ABBREVIATIONS: | |
| --- | --- |
| aq. | aqueous |
| DVS | dynamic vapor sorption |
| HV | high vacuum conditions |
| min | minutes |
| RH | relative humidity |

| LIST OF ABBREVIATIONS: | |
|---|---|
| r.t. | room temperature |
| V | volume |
| w | weight |
| XRD | X-ray powder diffraction |

X-ray diffraction patterns (XRD) were recorded on a Bruker D5000, using a Cu—K$_{alpha}$ (1.5418 Å) source, a 40 kV-30 mA generator, in a range of 3 et 40° (2theta). DVS is performed as gravimetric measurement (10-30 mg of sample), at a given temperature, under controlled relative humidity. Measurements are performed on a SMS (Surface Measurement Systems) DVS 1000. First, the sample is dried (0% RH) under dry nitrogen at the experiment temperature. Then a cycle of relative humidity (RH) is applied to the sample (generally increase by steps e.g. 20, 40, 60 and 80% RH and decrease to 0% RH by the same steps). The duration of each step of RH is sufficient to reach a weight equilibrium.

Example 1

1-[2-(4-Benzyl-4-hydroxy-piperidin-1-yl)-ethyl]-3-(2-methyl-quinolin-4-yl)-urea sulfate trihydrate 1-[2-(4-Benzyl-4-hydroxy-piperidin-1-yl)-ethyl]-3-(2-methyl-quinolin-4-yl)-urea (1 equivalent) is dissolved in ethanol at a concentration of 25% w/w and the mixture is heated at 50° C. Aqueous sulfuric acid (1M, 1.1 equivalents) is added. Optionally, the crystallization is initiated by a wet seed of Example 1 (0.5%). The suspension is cooled to 0° C. with a cooling rate of 15° C./h and maintained at this temperature at least 1 hour before filtration and washing with aqueous ethanol (50% W/W). The solid is dried at 30° C. under a wet stream of nitrogen (50% RH) to provide the title compound with a purity of 97.7% with a yield of approximately 90%.

X-ray Diffraction Pattern (XRD) of 1-[2-(4-benzyl-4-hydroxy-piperidin-1-yl)-ethyl]-3-(2-methyl-quinolin-4-yl)-urea Sulfate Trihydrate Described in Example 1

Figure 1:
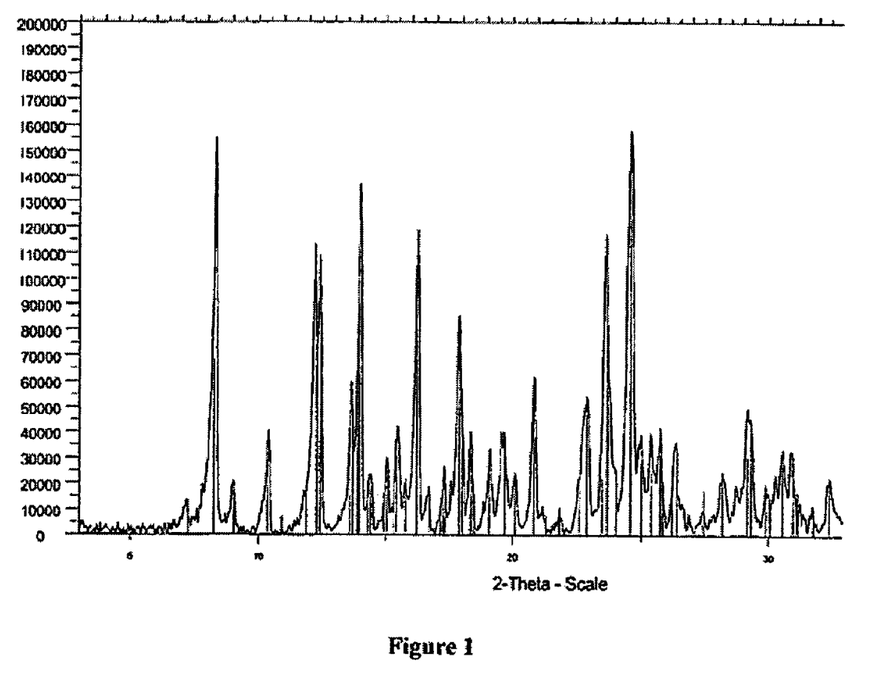

FIG. 1 shows the XRD-diffraction pattern of the compound described in Example 1. Table 1 summarizes the peaks and their intensity.

The parameters used to obtain these results were as follows:

Example 1 Type: 2Th/Th locked—Start: 3.000°—End: 40.000°—Step: 0.020°—Step time: 1 s—Temp.: 25° C. (room temperature)—Time Started: 3 s—2-Theta: 3.0000—Theta: 1.500°—Phi: 0.00°

DIF—Y: 77.31%—dxby: 1. —WL: 1.54056-0—

TABLE 1

2-Theta Angles and their intensities of the X-ray diffraction pattern (XRD) of the compound described in Example 1

| 2-Theta Angle [°] | d value [Angstrom] | Intensity [Count] | Intensity [%] |
|---|---|---|---|
| 7.214 | 12.244 | 10157 | 10.3 |
| 8.232 | 10.731 | 51311 | 52.2 |
| 9.013 | 9.803 | 12753 | 13 |
| 10.317 | 8.567 | 25230 | 25.7 |
| 10.899 | 8.111 | 5260 | 5.4 |
| 11.854 | 7.46 | 13398 | 13.6 |
| 12.276 | 7.204 | 58045 | 59.1 |
| 12.385 | 7.141 | 48973 | 49.9 |
| 13.559 | 6.525 | 22869 | 23.3 |

TABLE 1-continued

2-Theta Angles and their intensities of the X-ray diffraction pattern (XRD) of the compound described in Example 1

| 2-Theta Angle [°] | d value [Angstrom] | Intensity [Count] | Intensity [%] |
|---|---|---|---|
| 13.655 | 6.479 | 36267 | 36.9 |
| 13.832 | 6.397 | 42274 | 43 |
| 13.924 | 6.355 | 67326 | 68.5 |
| 14.267 | 6.203 | 15708 | 16 |
| 14.379 | 6.155 | 13167 | 13.4 |
| 14.894 | 5.943 | 11781 | 12 |
| 15.022 | 5.893 | 13629 | 13.9 |
| 15.312 | 5.782 | 12705 | 12.9 |
| 15.4 | 5.749 | 23092 | 23.5 |
| 15.762 | 5.618 | 16170 | 16.5 |
| 16.195 | 5.468 | 59851 | 60.9 |
| 16.7 | 5.304 | 13660 | 13.9 |
| 17.15 | 5.166 | 7580 | 7.7 |
| 17.242 | 5.139 | 11781 | 12 |
| 17.322 | 5.115 | 15708 | 16 |
| 17.88 | 4.957 | 55081 | 56.1 |
| 17.998 | 4.925 | 25179 | 25.6 |
| 18.34 | 4.833 | 22943 | 23.4 |
| 18.481 | 4.797 | 12936 | 13.2 |
| 19.076 | 4.649 | 18222 | 18.6 |
| 19.681 | 4.507 | 24880 | 25.3 |
| 20.08 | 4.418 | 14824 | 15.1 |
| 20.829 | 4.261 | 38203 | 38.9 |
| 21.32 | 4.164 | 5394 | 5.5 |
| 21.836 | 4.067 | 8044 | 8.2 |
| 22.614 | 3.929 | 13398 | 13.6 |
| 22.891 | 3.882 | 40775 | 41.5 |
| 23.483 | 3.785 | 16170 | 16.5 |
| 23.706 | 3.75 | 59467 | 60.5 |
| 24.046 | 3.698 | 18942 | 19.3 |
| 24.6 | 3.616 | 98226 | 100 |
| 25.011 | 3.557 | 21021 | 21.4 |
| 25.4 | 3.504 | 25257 | 25.7 |
| 25.76 | 3.456 | 23231 | 23.7 |
| 25.863 | 3.442 | 15246 | 15.5 |
| 26.217 | 3.396 | 10395 | 10.6 |
| 26.384 | 3.375 | 25209 | 25.7 |
| 27.449 | 3.247 | 13110 | 13.3 |
| 28.191 | 3.163 | 18423 | 18.8 |
| 29.144 | 3.062 | 22638 | 23 |
| 29.305 | 3.045 | 32340 | 32.9 |
| 29.9 | 2.986 | 12317 | 12.5 |
| 30.08 | 2.968 | 9631 | 9.8 |
| 30.56 | 2.923 | 19866 | 20.2 |
| 30.997 | 2.883 | 20289 | 20.7 |
| 31.155 | 2.868 | 12474 | 12.7 |
| 31.809 | 2.811 | 6865 | 7 |
| 32.444 | 2.757 | 14863 | 15.1 |
| 33.568 | 2.667 | 7444 | 7.6 |
| 35.804 | 2.506 | 6575 | 6.7 |
| 36.484 | 2.461 | 7120 | 7.2 |
| 37.241 | 2.412 | 12325 | 12.5 |
| 39.54 | 2.277 | 5676 | 5.8 |

It has to be understood that due to small changes in the experimental details, small deviations in the 2-Theta values of the characteristic peaks in the X-ray powder diffraction patterns may occur.

Crystal Structure Information of 1-[2-(4-benzyl-4-hydroxy-piperidin-1-yl)-ethyl]-3-(2-methyl-quinolin-4-yl)-urea sulfate trihydrate Described in Example 1

| Formula C25H38N4O9S1 | | |
|---|---|---|
| Crystal Class | Monoclinic | Space Group P 1 21/c 1 |
| a  9.90180(10) | alpha | 90.02 |
| b  11.62120(10) | beta | 92.1147(5) |
| c  24.4348(2) | gamma | 90.02 |

TABLE 2

DVS data of the compound described in Example 1

| Target | | Change In Mass (%) | | |
|---|---|---|---|---|
| | RH (%) | Sorption | Desorption | Hysteresis |
| Cycle 1 | 0.0 | 0.00 | −0.02 | |
| | 20.0 | 9.71 | 9.97 | 0.26 |
| | 40.0 | 10.23 | 10.26 | 0.03 |
| | 60.0 | 10.42 | 10.40 | −0.02 |
| | 85.0 | 10.68 | 10.68 | |
| Cycle 2 | 0.0 | −0.02 | −0.02 | |
| | 20.0 | 9.81 | 9.98 | 0.17 |
| | 40.0 | 10.26 | 10.28 | 0.02 |
| | 60.0 | 10.42 | 10.42 | 0.01 |
| | 85.0 | 10.68 | 10.68 | |

| | | | | Coordinates | | | | | | |
|---|---|---|---|---|---|---|---|---|---|---|
| S1  | 5 | 0.61225  | 0.30855  | 0.69926 | 1.00000 | 0.02322 | 0.02464 | 0.02313 | 0.00167 | 0.00063 | 0.00177 |
| O2  | 4 | 0.75650  | 0.31402  | 0.71730 | 1.00000 | 0.02586 | 0.03254 | 0.02979 | 0.00278 | −0.00447 | 0.00256 |
| O3  | 4 | 0.58955  | 0.38261  | 0.65118 | 1.00000 | 0.03122 | 0.04462 | 0.03211 | 0.01219 | −0.00409 | 0.00430 |
| O4  | 4 | 0.57966  | 0.18851  | 0.68588 | 1.00000 | 0.03488 | 0.02929 | 0.04629 | −0.00599 | 0.00578 | −0.00161 |
| O5  | 4 | 0.52793  | 0.35026  | 0.74402 | 1.00000 | 0.03548 | 0.03517 | 0.03507 | −0.00384 | 0.01084 | −0.00025 |
| C6  | 1 | 1.06055  | 0.14970  | 0.64896 | 1.00000 | 0.02454 | 0.02130 | 0.02257 | 0.00206 | 0.00058 | −0.00056 |
| C7  | 1 | 1.12232  | 0.24424  | 0.61313 | 1.00000 | 0.03172 | 0.02449 | 0.02891 | 0.00194 | 0.00403 | −0.00495 |
| C8  | 1 | 1.11753  | 0.21849  | 0.55275 | 1.00000 | 0.02995 | 0.02402 | 0.02877 | 0.00430 | 0.00426 | −0.00571 |
| C9  | 1 | 1.21317  | 0.14730  | 0.52949 | 1.00000 | 0.03226 | 0.02742 | 0.03788 | 0.00418 | 0.00723 | −0.00204 |
| C10 | 1 | 1.20706  | 0.12488  | 0.47335 | 1.00000 | 0.05040 | 0.02742 | 0.04308 | −0.00375 | 0.01655 | −0.00362 |
| C11 | 1 | 1.10561  | 0.17362  | 0.44020 | 1.00000 | 0.05518 | 0.03689 | 0.03007 | −0.00216 | 0.00308 | −0.01324 |
| C12 | 1 | 1.01004  | 0.24365  | 0.46248 | 1.00000 | 0.03887 | 0.03909 | 0.03499 | 0.00696 | −0.00108 | −0.00786 |
| C13 | 1 | 1.01638  | 0.26594  | 0.51861 | 1.00000 | 0.03167 | 0.03385 | 0.03080 | 0.00592 | 0.00465 | −0.00114 |
| C14 | 1 | 1.06064  | 0.19260  | 0.70839 | 1.00000 | 0.02371 | 0.02675 | 0.02450 | −0.00049 | −0.00073 | −0.00262 |
| C15 | 1 | 0.99245  | 0.10870  | 0.74596 | 1.00000 | 0.02345 | 0.02899 | 0.02040 | 0.00092 | −0.00158 | 0.00013 |
| N16 | 3 | 0.84909  | 0.08816  | 0.72582 | 1.00000 | 0.02198 | 0.02239 | 0.02046 | 0.00057 | 0.00103 | −0.00159 |
| C17 | 1 | 0.84692  | 0.03907  | 0.66903 | 1.00000 | 0.02489 | 0.02614 | 0.02038 | −0.00248 | 0.00158 | −0.00282 |
| C18 | 1 | 0.91619  | 0.12027  | 0.62983 | 1.00000 | 0.02443 | 0.02694 | 0.02117 | 0.00136 | 0.00007 | −0.00088 |
| C19 | 1 | 0.77287  | 0.01423  | 0.76410 | 1.00000 | 0.02965 | 0.02321 | 0.02425 | 0.00293 | 0.00416 | −0.00174 |
| C20 | 1 | 0.72630  | 0.08309  | 0.81299 | 1.00000 | 0.03694 | 0.02660 | 0.02164 | 0.00124 | 0.00755 | −0.00374 |
| N21 | 3 | 0.65520  | 0.00988  | 0.84999 | 1.00000 | 0.03150 | 0.03283 | 0.01998 | 0.00113 | 0.00270 | −0.00819 |
| C22 | 1 | 0.70082  | −0.00650 | 0.90231 | 1.00000 | 0.02529 | 0.02356 | 0.02126 | −0.00087 | 0.00274 | −0.00165 |
| N23 | 3 | 0.61239  | −0.07503 | 0.93170 | 1.00000 | 0.02335 | 0.02555 | 0.02022 | 0.00053 | 0.00116 | −0.00338 |
| C24 | 1 | 0.62202  | −0.09992 | 0.98648 | 1.00000 | 0.02275 | 0.02173 | 0.02082 | −0.00006 | 0.00294 | 0.00242 |
| C25 | 1 | 0.52400  | −0.17760 | 1.00846 | 1.00000 | 0.02295 | 0.02371 | 0.02385 | 0.00080 | 0.00346 | 0.00286 |
| C26 | 1 | 0.53177  | −0.20051 | 1.06518 | 1.00000 | 0.02457 | 0.02575 | 0.02287 | 0.00108 | 0.00249 | 0.00319 |
| N27 | 3 | 0.63200  | −0.14985 | 1.09755 | 1.00000 | 0.02772 | 0.03166 | 0.01952 | 0.00063 | 0.00208 | 0.00192 |
| C28 | 1 | 0.72600  | −0.08148 | 1.07716 | 1.00000 | 0.02478 | 0.03071 | 0.02230 | −0.00180 | 0.00144 | 0.00249 |
| C29 | 1 | 0.72175  | −0.05396 | 1.02179 | 1.00000 | 0.02536 | 0.02706 | 0.02325 | 0.00002 | 0.00233 | −0.00077 |
| C30 | 1 | 0.83455  | −0.03727 | 1.11567 | 1.00000 | 0.03160 | 0.04595 | 0.02380 | −0.00433 | −0.00394 | −0.00283 |
| C31 | 1 | 0.44021  | −0.27599 | 1.08943 | 1.00000 | 0.03315 | 0.03296 | 0.02721 | 0.00431 | 0.00675 | 0.00116 |
| C32 | 1 | 0.34335  | −0.33018 | 1.05725 | 1.00000 | 0.03354 | 0.03358 | 0.03909 | 0.00468 | 0.00903 | −0.00618 |
| C33 | 1 | 0.33499  | −0.30941 | 1.00057 | 1.00000 | 0.03129 | 0.03472 | 0.03698 | 0.00074 | 0.00063 | −0.00758 |
| C34 | 1 | 0.42228  | −0.23517 | 0.97654 | 1.00000 | 0.02790 | 0.02945 | 0.02830 | 0.00056 | 0.00076 | −0.00283 |
| O35 | 4 | 0.80651  | 0.03300  | 0.92140 | 1.00000 | 0.03090 | 0.04063 | 0.02968 | 0.00500 | 0.00135 | −0.01196 |
| O36 | 4 | 1.13670  | 0.04565  | 0.64500 | 1.00000 | 0.02594 | 0.02489 | 0.02898 | 0.00159 | 0.00165 | 0.00240 |
| O37 | 4 | 0.35801  | 0.20143  | 0.79365 | 1.00000 | 0.04596 | 0.05690 | 0.02594 | 0.00553 | 0.00357 | −0.01359 |
| O38 | 4 | 0.62759  | 0.54632  | 0.79414 | 1.00000 | 0.03006 | 0.03907 | 0.05616 | −0.01265 | −0.00524 | 0.00291 |
| O39 | 4 | 0.90339  | 0.32234  | 0.81772 | 1.00000 | 0.05421 | 0.02870 | 0.04454 | −0.00971 | −0.01512 | 0.00371 |

DVS of 1-[2-(4-benzyl-4-hydroxy-piperidin-1-yl)-ethyl]-3-(2-methyl-quinolin-4-yl)-urea sulfate trihydrate Described in Example 1

Table 2 summarizes the results of two cycles (0 to 85% relative humidity) in a DVS measurement (40° C.) of 1-[2-(4-benzyl-4-hydroxy-piperidin-1-yl)-ethyl]-3-(2-methyl-quinolin-4-yl)-urea sulfate trihydrate described in Example 1.

Example 2

1-[2-(4-Benzyl-4-hydroxy-piperidin-1-yl)-ethyl]-3-(2-methyl-quinolin-4-yl)-urea sulfate trihydrate To a suspension of 1-[2-(4-benzyl-4-hydroxy-piperidin-1-yl)-ethyl]-3-(2-methyl-quinolin-4-yl)-urea (21.36 kg) in $CH_3OH$ (178 L) is added aqueous $H_2SO_4$ (6 L, 9.91%) during 10 min. The clear solution is filtered and further aqueous $H_2SO_4$ (33.8 L, 1.07 M) is added during 45 min. The solution is cooled to −2° C. during 1.5 h and stirred at −5 to −9° C. for 1 h. The formed precipitate is filtered, washed with cooled CH₃OH (−5° C., 54 L) and dried under a stream of nitrogen provide 1-[2-(4-benzyl-4-hydroxy-piperidin-1-yl)-ethyl]-3-(2-methyl-quinolin-4-yl)-urea of formula I sulfate as a non-defined hydrate. A slurry of the so obtained salt in H₂O (16.2% w/w) is stirred for 3 days at 25° C. Filtration and drying at 30° C. under a wet stream of nitrogen (50% RH) provides the title compound.

X-Ray Diffraction Pattern (XRD) of 1-[2-(4-benzyl-4-hydroxy-piperidin-1-yl)-ethyl]-3-(2-methyl-quinolin-4-yl)-urea sulfate trihydrate Described in Example 2

Figure 2:
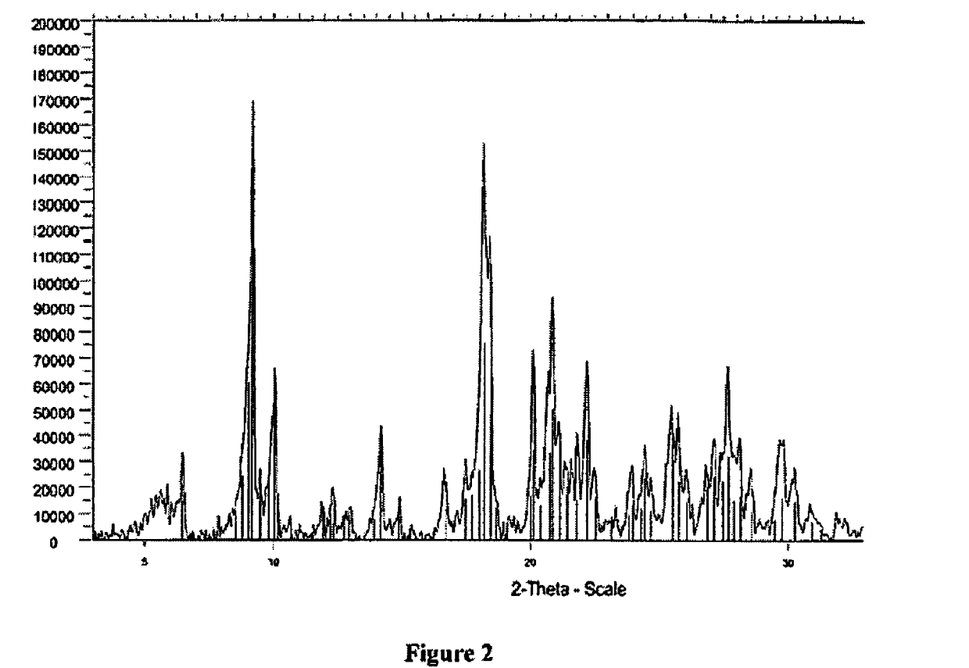

FIG. 2 shows the XRD-diffraction pattern of the compound described in Example 2. Table 3 summarizes the peaks and their intensity.

The parameters used to obtain these results were as follows:

Example 2 Type: 2Th/Th locked—Start: 3.000°—End: 40.000°—Step: 0.020°—Step time: 1 s—Temp.: 30° C.—Time Started: 3 s—2-Theta: 3.000°—Theta: 1.500°—Phi: 0.00°—Aux1: 0.0

DIF—Y: 77.08%—dxby: 1. —WL: 1.54056-0—

TABLE 3

2-Theta Angles and their intensities of the X-ray diffraction pattern (XRD) of the compound described in Example 2

| 2-Theta Angle [°] | d value [Angstrom] | Intensity [Count] | Intensity [%] |
| --- | --- | --- | --- |
| 6.405 | 13.788 | 20831 | 16 |
| 8.503 | 10.39 | 10816 | 8.3 |
| 8.755 | 10.092 | 24436 | 18.7 |
| 8.984 | 9.835 | 60489 | 46.3 |
| 9.137 | 9.671 | 130592 | 100 |
| 9.461 | 9.34 | 26839 | 20.6 |
| 9.784 | 9.033 | 24836 | 19 |
| 9.974 | 8.861 | 66097 | 50.6 |
| 10.15 | 8.708 | 17626 | 13.5 |
| 10.627 | 8.318 | 6810 | 5.2 |
| 11.897 | 7.433 | 12418 | 9.5 |
| 12.214 | 7.24 | 9614 | 7.4 |
| 12.316 | 7.181 | 12018 | 9.2 |
| 12.704 | 6.963 | 8412 | 6.4 |
| 12.907 | 6.853 | 9214 | 7.1 |
| 13.866 | 6.381 | 7611 | 5.8 |
| 14.12 | 6.267 | 34050 | 26.1 |
| 14.821 | 5.972 | 12819 | 9.8 |
| 15.259 | 5.802 | 4006 | 3.1 |
| 16.686 | 5.309 | 11617 | 8.9 |
| 17.434 | 5.082 | 15623 | 12 |
| 17.679 | 5.013 | 17225 | 13.2 |
| 17.964 | 4.934 | 26439 | 20.2 |
| 18.162 | 4.88 | 76112 | 58.3 |
| 18.402 | 4.817 | 49272 | 37.7 |
| 18.617 | 4.762 | 12018 | 9.2 |
| 19.045 | 4.656 | 5208 | 4 |
| 19.983 | 4.44 | 16825 | 12.9 |
| 20.09 | 4.416 | 34451 | 26.4 |
| 20.371 | 4.356 | 13219 | 10.1 |
| 20.717 | 4.284 | 32848 | 25.2 |
| 20.822 | 4.263 | 50474 | 38.7 |
| 21.105 | 4.206 | 30445 | 23.3 |
| 21.41 | 4.147 | 20831 | 16 |
| 21.777 | 4.078 | 15222 | 11.7 |
| 22.157 | 4.009 | 38456 | 29.4 |
| 22.501 | 3.948 | 16024 | 12.3 |
| 23.121 | 3.844 | 6409 | 4.9 |
| 23.817 | 3.733 | 9614 | 7.4 |
| 23.959 | 3.711 | 13620 | 10.4 |
| 24.286 | 3.662 | 11617 | 8.9 |
| 24.435 | 3.64 | 23635 | 18.1 |
| 24.653 | 3.608 | 11216 | 8.6 |
| 25.492 | 3.491 | 40059 | 30.7 |
| 25.733 | 3.459 | 22032 | 16.9 |
| 26.039 | 3.419 | 14421 | 11 |
| 26.855 | 3.317 | 20029 | 15.3 |
| 27.104 | 3.287 | 24035 | 18.4 |
| 27.446 | 3.247 | 22032 | 16.9 |
| 27.657 | 3.223 | 31646 | 24.2 |
| 27.874 | 3.198 | 14822 | 11.3 |
| 28.119 | 3.171 | 17225 | 13.2 |
| 28.518 | 3.127 | 10415 | 8 |
| 29.444 | 3.031 | 7211 | 5.5 |
| 29.722 | 3.003 | 16024 | 12.3 |
| 30.224 | 2.955 | 14421 | 11 |
| 30.898 | 2.892 | 6409 | 4.9 |
| 31.262 | 2.859 | 4406 | 3.4 |
| 33.903 | 2.642 | 7611 | 5.8 |
| 34.338 | 2.609 | 5608 | 4.3 |
| 34.902 | 2.569 | 6409 | 4.9 |
| 36.09 | 2.487 | 11617 | 8.9 |
| 37.546 | 2.394 | 8813 | 6.7 |
| 37.703 | 2.384 | 6409 | 4.9 |
| 38.561 | 2.333 | 4406 | 3.4 |
| 39.436 | 2.283 | 3205 | 2.5 |
| 39.823 | 2.262 | 3605 | 2.8 |

DVS of 1-[2-(4-benzyl-4-hydroxy-piperidin-1-yl)-ethyl]-3-(2-methyl-quinolin-4-yl)-urea sulfate trihydrate Described in Example 2

Table 4 summarizes the results of three cycles (0 to 85% relative humidity) in a DVS measurement (25° C.) of 1-[2-(4-benzyl-4-hydroxy-piperidin-1-yl)-ethyl]-3-(2-methyl-quinolin-4-yl)-urea sulfate trihydrate described in Example 2.

TABLE 4

DVS data of the compound described in Example 2

| | Target | Change In Mass (%) | | |
| --- | --- | --- | --- | --- |
| | RH (%) | Sorption | Desorption | Hysteresis |
| Cycle 1 | 0.0 | 0.00 | −0.01 | |
| | 20.0 | 11.38 | 11.94 | 0.57 |
| | 40.0 | 12.00 | 12.31 | 0.32 |
| | 60.0 | 12.41 | 12.49 | 0.08 |
| | 85.0 | 12.70 | 12.70 | |
| Cycle 2 | 0.0 | −0.01 | 0.00 | |
| | 20.0 | 11.52 | 11.95 | 0.43 |
| | 40.0 | 12.06 | 12.32 | 0.25 |
| | 60.0 | 12.41 | 12.49 | 0.07 |
| | 85.0 | 12.70 | 12.70 | |
| Cycle 3 | 0.0 | 0.00 | 0.08 | |
| | 20.0 | 11.55 | | |
| | 40.0 | 12.07 | | |
| | 60.0 | 12.40 | | |
| | 85.0 | 12.69 | 12.69 | |

Example 3

1-[2-(4-Benzyl-4-hydroxy-piperidin-1-yl)-ethyl]-3-(2-methyl-quinolin-4-yl)-urea sulfate dihydrate To a suspension of 1-[2-(4-benzyl-4-hydroxy-piperidin-1-yl)-ethyl]-3-(2-methyl-quinolin-4-yl)-urea (21.36 kg) in CH₃OH (178 L) is added aqueous H₂SO₄ (6 L, 9.91%) during 10 min. The clear solution is filtered and further aqueous H₂SO₄ (33.8 L, 1.07 M) is added during 45 min. The solution is cooled to −2° C. during 1.5 h and stirred at −5 to −9° C. for 1 h. The formed precipitate is filtered, washed with cooled CH₃OH (−5° C., 54 L) and dried under a stream of nitrogen provide 1-[2-(4-benzyl-4-hydroxy-piperidin-1-yl)-ethyl]-3-(2-methyl-quinolin-4-yl)-urea of formula I sulfate as a non-defined hydrate. The so obtained salt is exposed to humid atmosphere (>70% RH) at 25° C. to provide the title compound.

X-Ray Diffraction Pattern (XRD) of 1-[2-(4-benzyl-4-hydroxy-piperidin-1-yl)-ethyl]-3-(2-methyl-quinolin-4-yl)-urea sulfate trihydrate Described in Example 3

Figure 3:
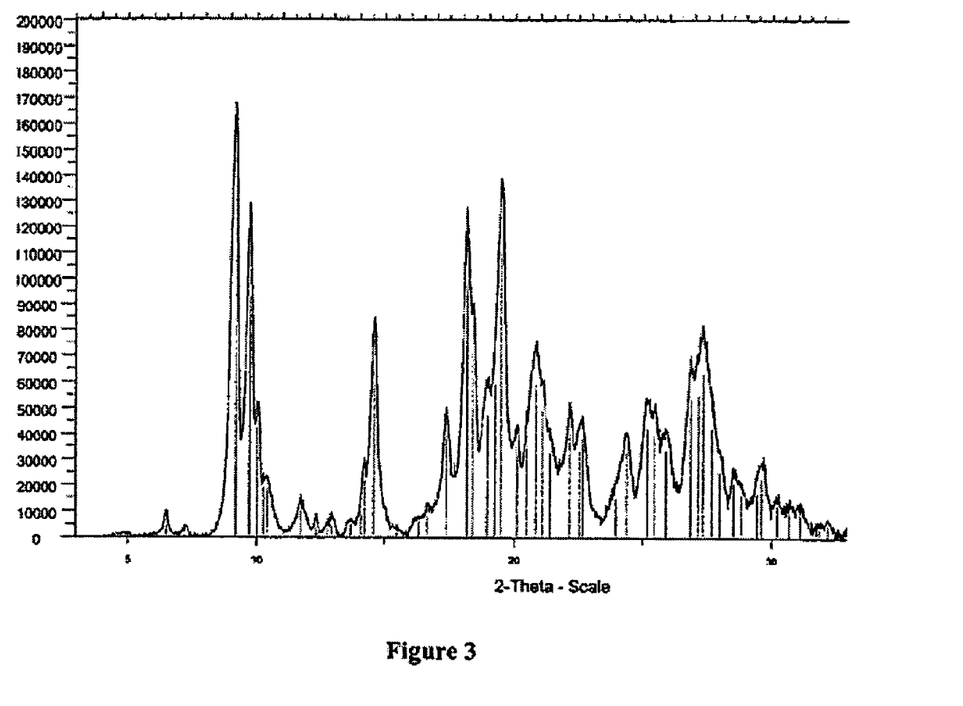

FIG. 3 shows the XRD-diffraction pattern of the compound described in Example 3. Table 5 summarizes the peaks and their intensity.

The parameters used to obtain these results were as follows:

Example 3 Type: 2Th/Th locked—Start: 4.0100—End: 40.0100—Step: 0.0200—Step time: 1 s—Temp.: 25° C. (room temperature)—Time Started: 0 s—2-Theta: 4.010° DIF—Y: 79.17%—d×by: 1.-WL: 1.54056-0—

TABLE 5

2-Theta Angles and their intensities of the X-ray diffraction pattern (XRD) of the compound described in Example 3

| 2-Theta Angle [°] | d value [Angstrom] | Intensity [Count] | Intensity [%] |
|---|---|---|---|
| 6.466 | 13.659 | 7918 | 5.9 |
| 7.197 | 12.273 | 3329 | 2.5 |
| 9.166 | 9.641 | 133099 | 100 |
| 9.696 | 9.115 | 102939 | 77.3 |
| 9.997 | 8.841 | 41811 | 31.4 |
| 10.238 | 8.634 | 18611 | 14 |
| 10.369 | 8.524 | 18712 | 14.1 |
| 11.693 | 7.562 | 12558 | 9.4 |
| 12.307 | 7.186 | 6910 | 5.2 |
| 12.736 | 6.945 | 4590 | 3.4 |
| 12.907 | 6.854 | 7313 | 5.5 |
| 13.644 | 6.485 | 5195 | 3.9 |
| 14.044 | 6.301 | 11600 | 8.7 |
| 14.188 | 6.237 | 23906 | 18 |
| 14.554 | 6.081 | 65465 | 49.2 |
| 15.449 | 5.731 | 3581 | 2.7 |
| 16.309 | 5.431 | 6506 | 4.9 |
| 16.621 | 5.329 | 10894 | 8.2 |
| 17.364 | 5.103 | 39642 | 29.8 |
| 18.164 | 4.88 | 100871 | 75.8 |
| 18.368 | 4.826 | 72375 | 54.4 |
| 18.949 | 4.68 | 47561 | 35.7 |
| 19.247 | 4.608 | 59009 | 44.3 |
| 19.48 | 4.553 | 110151 | 82.8 |
| 20.09 | 4.416 | 34750 | 26.1 |
| 20.451 | 4.339 | 38987 | 29.3 |
| 20.8 | 4.267 | 58556 | 44 |
| 21.065 | 4.214 | 48468 | 36.4 |
| 21.355 | 4.158 | 31976 | 24 |
| 22.126 | 4.014 | 41155 | 30.9 |
| 22.511 | 3.947 | 32682 | 24.6 |
| 22.655 | 3.922 | 37574 | 28.2 |
| 23.944 | 3.713 | 14425 | 10.8 |
| 24.373 | 3.649 | 32430 | 24.4 |
| 25.179 | 3.534 | 41962 | 31.5 |
| 25.45 | 3.497 | 39340 | 29.6 |
| 25.902 | 3.437 | 33287 | 25 |
| 26.859 | 3.317 | 53411 | 40.1 |
| 27.16 | 3.281 | 55126 | 41.4 |
| 27.365 | 3.257 | 63599 | 47.8 |
| 27.702 | 3.218 | 42164 | 31.7 |
| 27.991 | 3.185 | 24915 | 18.7 |
| 28.521 | 3.127 | 21082 | 15.8 |
| 28.834 | 3.094 | 16139 | 12.1 |
| 29.448 | 3.031 | 16492 | 12.4 |
| 29.623 | 3.013 | 22646 | 17 |
| 30.243 | 2.953 | 12458 | 9.4 |
| 30.7 | 2.91 | 10188 | 7.7 |
| 31.107 | 2.873 | 10844 | 8.1 |
| 31.863 | 2.806 | 4842 | 3.6 |
| 32.211 | 2.777 | 5447 | 4.1 |
| 33.279 | 2.69 | 12962 | 9.7 |
| 33.848 | 2.646 | 13517 | 10.2 |
| 34.867 | 2.571 | 10037 | 7.5 |
| 35.632 | 2.518 | 5951 | 4.5 |
| 35.927 | 2.498 | 8776 | 6.6 |
| 36.609 | 2.453 | 10440 | 7.8 |
| 37.142 | 2.419 | 8070 | 6.1 |
| 37.476 | 2.398 | 14475 | 10.9 |
| 38.748 | 2.322 | 12508 | 9.4 |
| 39.201 | 2.296 | 12962 | 9.7 |
| 39.607 | 2.274 | 6456 | 4.9 |

Example 4

1-[2-(4-Benzyl-4-hydroxy-piperidin-1-yl)-ethyl]-3-(2-methyl-quinolin-4-yl)-urea sulfate trihydrate 1-[2-(4-benzyl-4-hydroxy-piperidin-1-yl)-ethyl]-3-(2-methyl-quinolin-4-yl)-urea (15.4 kg, 1 equivalent) is dissolved in ethanol (78 L) and the mixture is heated at 50° C. Aqueous sulfuric acid (1M, 1.1 equivalents) is added during 35 minutes. The crystallization is initiated by a wet seed of Example 1 (1%) as described below. The suspension is cooled to 1° C. with a cooling rate of 14° C./h and maintained at this temperature at least 11 hours before filtration and washing with aqueous ethanol (50% W/W, 50 L). The solid is dried at 30° C. under a wet stream of nitrogen (33-40% RH) to provide the title compound with a purity of 99.4% with a yield of approximately 79%.

The wet seed used in the above procedure is prepared by mixing 1-[2-(4-benzyl-4-hydroxy-piperidin-1-yl)-ethyl]-3-(2-methyl-quinolin-4-yl)-urea sulfate trihydrate (Example 1, 104 g) with a saturated solution (421 g) of 1-[2-(4-benzyl-4-hydroxy-piperidin-1-yl)-ethyl]-3-(2-methyl-quinolin-4-yl)-urea sulfate trihydrate (Example 1, 73.9 g) in aqueous ethanol (50% W/W, 810 g).

Example 5

1-[2-(4-Benzyl-4-hydroxy-piperidin-1-yl)-ethyl]-3-(2-methyl-quinolin-4-yl)-urea sulfate trihydrate

1-[2-(4-Benzyl-4-hydroxy-piperidin-1-yl)-ethyl]-3-(2-methyl-quinolin-4-yl)-urea (1.01 kg, 1 equivalent) is dissolved in ethanol (3.05 kg) under stirring (200±20 rpm) and the mixture is heated at 50° C. Aqueous sulfuric acid (1M, 1.1 equivalents) is added during 20 minutes. The crystallization is initiated by a wet seed of Example 1 (1%) as described below. The obtained mixture is maintained at 50° C. for about 15 minutes, then it is cooled to 0° C. with a cooling rate of 15° C./h and maintained at this temperature for least 1 hour before filtration and washing with aqueous ethanol (50% W/W, 3 kg). The solid is dried in a conductive agitated dryer at a temperature of 35±3° C. under a wet stream of nitrogen (45±5% RH), optionally under stirring (max. 70 rpm) in case the cake humidity is below 25%, to provide the title compound with a purity of 99.8% with a yield of approximately 94%.

The wet seed used in the above procedure is added in two shots and is prepared by mixing 1-[2-(4-benzyl-4-hydroxy-piperidin-1-yl)-ethyl]-3-(2-methyl-quinolin-4-yl)-urea sulfate trihydrate (Example 1, 6.5 g) with a saturated solution (13.9 g for the first shot, plus 15.6 g for subsequent rinsing and second shot) of 1-[2-(4-benzyl-4-hydroxy-piperidin-1-yl)-ethyl]-3-(2-methyl-quinolin-4-yl)-urea sulfate trihydrate (Example 1, 7.0 g) in aqueous ethanol (50% W/W, 50.0 g) for about 2 minutes. The first shot of wet seed is prepared at least 5 minutes before use to ensure that the seed is correctly wetted.

The invention claimed is:

1. 1-[2-(4-benzyl-4-hydroxy-piperidin-1-yl)-ethyl]-3-(2-methyl-quinolin-4-yl)-urea of formula I,

I as a sulfate salt which is a crystalline mono-sulfate trihydrate.

2. Crystalline 1-[2-(4-benzyl-4-hydroxy-piperidin-1-yl)-ethyl]-3-(2-methyl-quinolin-4-yl)-urea mono-sulfate trihydrate according to claim 1 having an X-ray powder diffraction pattern as depicted in FIG. 1, wherein the X-ray diffraction pattern is recorded using a Cu—K$_{alpha}$ (1.5418 Å) source.

3. Crystalline 1-[2-(4-benzyl-4-hydroxy-piperidin-1-yl)-ethyl]-3-(2-methyl-quinolin-4-yl)-urea mono-sulfate trihydrate according to claim 1, wherein said crystalline form is characterized by the presence of peaks in an X-ray powder diffraction diagram at the following angles of refraction 2-Theta: 7.214°; 8.232°; 9.013°; 10.317°; 10.899°; 11.854°; 12.276°; 12.385°; 13.559°; 13.655°; 13.832°; 13.924°; 14.267°; 14.379°; 14.894°; 15.022°; 15.312°; 15.4°; 15.762°; 16.195°; 16.7°; 17.15°; 17.242°; 17.322°; 17.88°; 17.998°; 18.34°; 18.481°; 19.076°; 19.681°; 20.08°; 20.829°; 21.32°; 21.836°; 22.614°; 22.891°; 23.483°; 23.706°; 24.046°; 24.6°; 25.011"; 25.4°; 25.76°; 25.863°; 26.217°; 26.384°; 27.449°; 28.191°; 29.144°; 29.305°; 29.9°; 30.08°; 30.56°; 30.997°; 31.155°; 31.809°; 32.444°; 33.568°; 35.804°; 36.484°; 37.241°; and 39.54°, wherein the X-ray diffraction pattern is recorded using a Cu—K$_{alpha}$ (1.5418 Å) source and 2-Theta values are stated using Cu K$_{alpha1}$ radiation (1.5406 Å).

4. Crystalline 1-[2-(4-benzyl-4-hydroxy-piperidin-1-yl)-ethyl]-3-(2-methyl-quinolin-4-yl)-urea mono-sulfate trihydrate according to claim 1 wherein said crystalline form is characterized by the presence of peaks in an X-ray powder diffraction diagram at the following angles of refraction 2-Theta: 8.2°; 13.9°; 16.2°; 20.8°; 23.7°; and 24.6°, wherein the X-ray diffraction pattern is recorded using a Cu—K$_{alpha}$ (1.5418 Å) source and 2-Theta values are stated using Cu K$_{alpha1}$ radiation (1.5406 Å).

* * * * *